United States Patent [19]

Minassian et al.

[11] Patent Number: 5,254,457
[45] Date of Patent: Oct. 19, 1993

[54] MONOCLONAL ANTIBODIES AND METHOD FOR IDENTIFYING DIFFERENT AIDS-RELATED VIRUSES

[75] Inventors: Anton A. Minassian, Sotia, Burma; Mikulas Popovic; Robert C. Gallo, both of Bethesda, Md.

[73] Assignee: The United States of America as represented by the Secretary of the Department of Health and Human Services, Washington, D.C.

[21] Appl. No.: 295,933

[22] Filed: Jan. 11, 1989

[51] Int. Cl.[5] .......................... C12Q 1/70; C12N 5/00; A61K 35/14; C07K 3/00
[52] U.S. Cl. .................................. 435/5; 435/974; 435/7.2; 435/7.92; 435/7.93; 435/7.95; 435/975; 435/240.27; 530/388.35; 530/387.1
[58] Field of Search ............... 530/387, 388.35, 387.1; 435/5, 240.27, 974, 7.2, 7.92, 7.93, 7.94, 7.95, 974, 975, 240.27

[56] References Cited

U.S. PATENT DOCUMENTS 4,983,529  1/1991  Stewart et al. .................. 435/5
5,116,740  5/1992  Sarngadharan et al. .......... 435/5

OTHER PUBLICATIONS

Guyder et al, "Genome organization and transactivation of the human immunodeficiency virus type 2," Nature 326 (1987) 662-669.

Chakrabarti et al, "Sequence of simian immunodeficiency virus from macaque and its relationship to other human and simian viruses", Nature 328 (1987) 543-547.

Niedrig et al, "Monoclonal Antibodies Directed Against Human Immunodeficiency Virus (HIV) gag Proteins with Specificity for conserved Epitopes in HIV-1, HIV-2 and Simian Immunodeficiency Virus" J. Gen. Virol. 69 (1988) 2109-2114.

Ratner et al, "Complete nucleotide sequence of the AIDS virus, HTLV-III" Nature, 313 (1985) 277-284.

Alizon et al, "Genetic Variability of the AIDS virus; Nucleotide Sequence Analysis of Two Isolates from African Patients," Cell 46 (1986) 63-74.

Primary Examiner—Christine M. Nucker
Assistant Examiner—David R. Preston
Attorney, Agent, or Firm—Cushman, Darby & Cushman

[57] ABSTRACT

Novel hybridoma cell lines and monoclonal antibodies are provided which can differentiate between HIV-1, HIV-2 and SIV retrovirus isolates. A synthetic peptide which is useful as a universal diagnostic reagent for detecting retroviral infection is also described.

5 Claims, 4 Drawing Sheets

FIG. IA
FIG. IB

FIG. IC
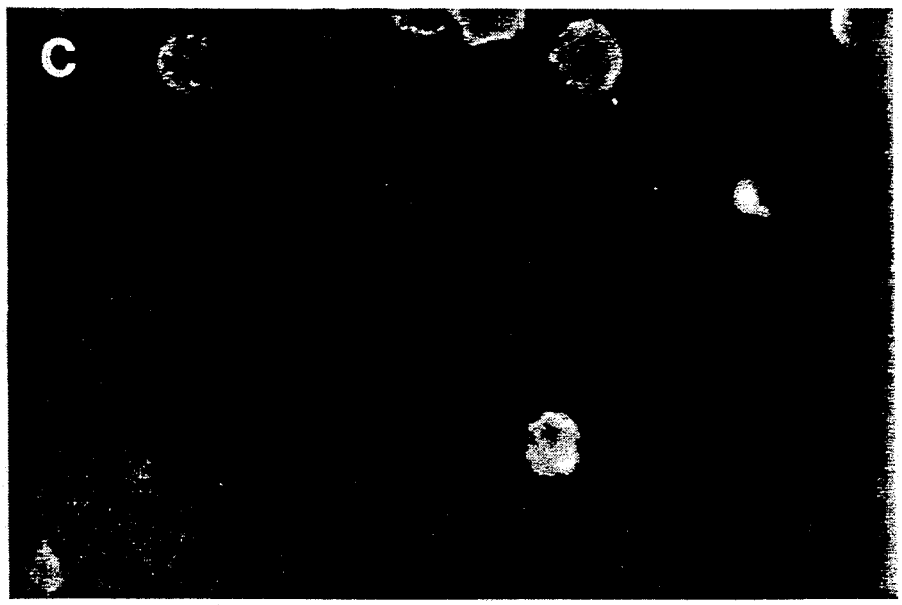
FIG. ID

MONOCLONAL ANTIBODIES AND METHOD FOR IDENTIFYING DIFFERENT AIDS-RELATED VIRUSES

The present invention is generally related to the development of reagents for simple and rapid identification of different isolates of AIDS-related viruses. More particularly, the present invention is related to the development of hybridomas secreting monoclonal antibodies against HIV-2 core proteins which are able to discriminate and identify HIV-1, HIV-2 and SIV isolates, and to provide a synthetic peptide which recognizes any member of HIV-1, HIV-2 and SIV family of viruses.

BACKGROUND OF THE INVENTION

Since the determination of human immunodeficiency virus type 1 (HIV-1) as the etiological agent of the acquired immunodeficiency syndrome (AIDS), several other retroviruses have been identified which share many structural, biological, genetic and antigenic properties with HIV-1. However, there are also significant differences in pathogenicity among these retroviruses. Of course, in order to understand various similarities and differences, the mode of transmission and the pathogenicity of these retorviruses, it is essential that specific reagents which rapidly identify and differentiate between various isolates of these retroviruses be readily available. Conventional molecular genetic methods currently employed for this purpose are expensive and time consuming, and the available commercial tests for HIV-1 recognize less than 50% of HIV-2 and SIV sera and vice versa.

SUMMARY OF THE INVENTION

It is, therefore, an object of the present invention to provide a set of monoclonal antibodies which, in a simple manner, rapidly discriminate and identify different AIDS-related viruses.

It is a further object of the present invention to describe an epitope which is common to all human and simian immuno-deficiency viruses and to provide a universal diagnostic test comprising a synthetic peptide composed of amino acid residues 226 to 237 of the HIV-1 gag gene, said synthetic peptide recognizing any member of the HIV-1, HIV-2 and SIV family of retroviruses.

It is another object of the present invention to provide a method for distinguishing between HIV-1, HIV-2 and SIV viruses and detecting the simultaneous presence of both HIV-1 and HIV-2 viruses in the same sample.

Other objects and advantages will become apparent from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1 shows the immunofluorescence reactivity of the R1C7 mAb with uninfected HUT-78 cells (A), HIV-2$_{NIH-Z}$-infected HUT-78 cells (B), HTLV-III$_B$-infected H9 cells (C) and STLV-III$_{AGM}$-infected HUT-78 cells (D).

FIG. 2 shows the results of immunological blot analysis of mAbs and human sera. Electrophoretically separated HIV-2$_{NIH-Z}$ (A), HTLV-III$_B$ (B), and STLV-III$_{AGM}$ (C) proteins were blotted onto nitrocellulose and were reacted with R5C4 (lane 1), R5F6 (land 2), A4F6 (lane 3), R1C7 (lane 4); HIV-1-positive serum (lane 5), negative control serum (lane 6), or HIV-2-positive serum (lane 7).

DETAILED DESCRIPTION OF THE INVENTION

The above and various other objects and advantages of the present invention are achieved by a group of hybridoma cell lines secreting monoclonal antibodies (mAbs) designated herein as R1C7, A4F6, R5C4 and R5F6, and by a synthetic peptide formed by amino acid residues 226-237 of the HIV-1 gag gene.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

MATERIALS AND METHODS

Cells and Viruses

Viruses were propagated in the human T-cell line HUT-78 or in the H9 clone. The HIV-1 isolates [human T-cell leukemia/lymphoma virus (HTLV)-III$_B$, HTLV-III$_{MN}$, HTLV-III$_{CC}$, HTLV-III$_{RF}$, and HTLV-III$_{Rutz}$] have been previously described (Popovic et al, 1984, *Science* 224, 497–500, Popovic et al, 1987, in *Viruses and Human Cancer*, eds. Gallo et al (Liss, New York), pp. 161–176). The HIV-2 strain used for immunization was isolated from the peripheral blood lymphocytes of an AIDS patient and was designated HIV-2$_{NIH-Z}$ (Zagury et al, 1988, *Proc. Natl. Acad. Sci. USA* 85, 5941–5945). This isolate is serologically very similar to the LAV-2$_{Rod}$ isolate previously described (Clavel et al, 1986, *Science* 233, 343–346). Fixed cells of the HUT-78 cell line infected with the LAV-2$_{Rod}$ isolate were provided by E. M. Fenyo (Karolinska Institute, Stockholm). Another HIV-2 isolate, termed LK001 ST9, from a healthy West African individual was provided by B. Hahn and G. Shaw (University of Alabama, Birmingham, Ala.). Slides with fixed HUT-78 cells infected with the SIV isolates 142, 157, 186, 251, and 309, recovered from rhesus macaques (*Macaca mulatta*), were provided by M. D. Daniel and R. Desrosiers (New England Regional Primate Research Center, Harvard Medical School, Southboro, Mass.). The SIV isolates, simian T-cell leukemia/lymphoma virus (STLV)-III$_{AGM}$ and HT-SIV/SMM-5, from an African green monkey and a sooty mangabey (*Cercocebus atys*), were provided by M. Essex (Harvard School of Public Health, Boston) and P. Fultz (Center for Disease Control, Atlanta), respectively. Equine infectious anemia virus propagated in equine fetal kidney cells was provided by R. W. Johnson (Biological Carcinogenesis Program, Frederick Cancer Research Facility, Frederick, MD). HTLV-I was grown in human cord blood T cells (C91/PL) as described in Popovic et al (1983) *Science* 219, 856-859.

Immunization, Cell Fusion, and Establishment of Hybridoma Clones

The viruses used in the study were purified by banding twice in sucrose gradients. HIV-2$_{NIH-Z}$ virus was disrupted with 0.5% Triton X-100 in 0.6M NaCl and was dialyzed overnight against phosphate-buffered saline (PBS). Four mice were immunized intraperitoneally with 1 ml of solubilized virus emulsified in complete Freund's adjuvant on day 0 and the same amount of antigen in PBS on days 1, 2, 16, 17, and 18. Each mouse received the equivalent of $1 \times 10^{10}$ virus particles each immunization. Three days after the last injection, the splenocytes of the animal with the highest serum antibody titer were fused with Sp2 myeloma cells according to a standard protocol described in Galfre et al (1977) *Nature* (London) 266, 550-554. Ten to 14 days after fusion, supernatants of hybrids growing in hypoxanthine/aminopterin/thymidine medium were tested for specific antibody production by the immunofluorescence technique described below. Hybridomas secreting antibodies reactive against HIV-2 were subcloned by limiting dilution. Cells were plated at a concentration of 0.5 cell per well in round bottom 96-well microplates. To increase plating efficiency of these cells, conditioned culture fluids harvested from Sp2 cells were included in the hypoxanthine/aminopterin/thymidine culture medium.

Immunofluorescence and Other Immunological Assays

The standard indirect immunofluorescence assay was carried out on fixed cells as described in Robert-Guroff et al (1982) *Science* 215, 975-978. Briefly, uninfected and infected HUT-78 and H9 cells were spotted on slides, air-dried, and fixed for 10 min in acetone/methanol, 1:1 (vol/vol). Supernatant (10 μl) to be tested was applied and incubated 30 min at room temperature (22°-25° C.). Fluorescein-conjugated goat anti-mouse immunoglobulin (IgA, IgM, and IgG) (Cappel Laboratories, Cochranville, Pa.) was the second antibody. In some cases, hybridoma supernatants were tested for specific anti-HIV-2 antibodies by using a spot-immunofluorescence technique. Class and subclass determinations of immunoglobulins secreted by hybridomas were performed by using the Ouchterlony technique with specific anti-mouse immunoglobulin typing sera (Calbiochem). For detection of HIV-1 core proteins, two previously described mAbs, designated BT3 and M33, were used (di Marzo et al, 1985, *Science* 228, 5199-5202).

Immunological Blot Assay

Viral proteins were separated from sucrose gradient-banded HIV-1, HIV-2, and SIV by sodium dodecyl sulfate/polyacrylamide gel electrophoresis and were blotted onto a nitrocellulose sheet according to Towbin et al (1979) *Proc. Natl. Acad. Sci. USA* 76, 4350-4353. The blots were reacted with each mAb as well as with HIV-1 and HIV-2 positive and negative control human sera (Sarngadharan et al, 1985, *Cancer Res.* Suppl. 45, 4574-4577).

RESULTS

Development and Characterization of mAbs. Out of 118 individual hybridomas that grew in hypoxanthine/aminopterin/thymidine medium, 48 secreted antibodies reactive with HIV-2$_{NIH-Z}$-infected HUT-78 cells. However, 44 of these also reacted with uninfected HUT-78 cells, which clearly demonstrated that the antigen used for immunization contained material originating from the cells that were used for propagation of the virus. Four hybridomas reacted with HIV-2$_{NIH-Z}$-infected HUT-78 cells but lacked reactivity with uninfected HUT-78 cells and were, therefore, considered virus-specific. These hybridomas were cloned twice and were designated R1C7, A4F6, R5C4, and R5F6. They continue to secrete specific antibodies 2 years after fusion. All four are of the IgG1 subclass as determined by the Ouchterlony technique by using class- —and subclass—specific anti-mouse immunoglobin typing antisera.

Reactivity of mAbs with HIV-1, HIV-2, and SIV Isolates

The four anti-HIV-2$_{NIH-Z}$ mAbs were tested for reactivity with cells infected with different HIV-1, HIV-2, and SIV isolates by using an indirect immunofluorescence assay. Negative control cell populations included uninfected HUT-78 and H9 cells, HTLV-1-infected cord blood T cells (C91/PL), and equine infectious anemia virus-infected equine fetal kidney cells. For detection of HIV-1-infected cells, two previously characterized mAbs directed against the CA protein (BT3) and MA protein (M33) of HIV-1 were included in this study. An example of immunofluorescence reactivity of the most broadly reactive mAb raised against HIV-2$_{NIH-Z}$, designated R1C7, is shown in FIG. 1. This antibody exhibited strong positivity with HUT-78 cells infected with HIV-2$_{NIH-Z}$ or STLV-III$_{AGM}$ and also with H9 cells infected with HTLV-III$_B$, but not with uninfected HUT-78 cells (FIG. 1). The data from an extensive survey of immunofluorescence reactivities with various isolates are summarized in Table 1. The antibody R1C7 reacted with all HIV-1, HIV-2 and SIV isolates tested thus far. The A4F6 mAb reacted with members of the HIV-2 group (HIV-2$_{NIH-Z}$, LK001 St9, and LAV-2$_{Rod}$) and also with some SIV isolates (STLV-III$_{AGM}$, SIV-251, and Siv-309), but not with HIV-1 isolates. The R5C4 and R5F6 mAbs were strongly reactive with the HIV-2$_{NIH-Z}$, LK001 ST9, and LAV-2$_{Rod}$ isolates. None of these four mAbs reacted with uninfected H9 or HUT-78 cells or with HTLV-I or equine infectious anemia virus-infected cells. Similarly, the mAbs BT3 and M33 directed against HIV-1 core proteins reacted only with cells infected with HIV-1 isolates. It may be noted that both the R1C7 and A4F6 mAbs against the HIV-2 CA protein) reacted with fixed cells but not with live cells, whereas R5C4 and R5F6 (directed against the HIV-2 MA protein) reacted with fixed as well as live cells.

Identification of Viral Proteins Reacting with mAbs

Figures 2A, 2B:
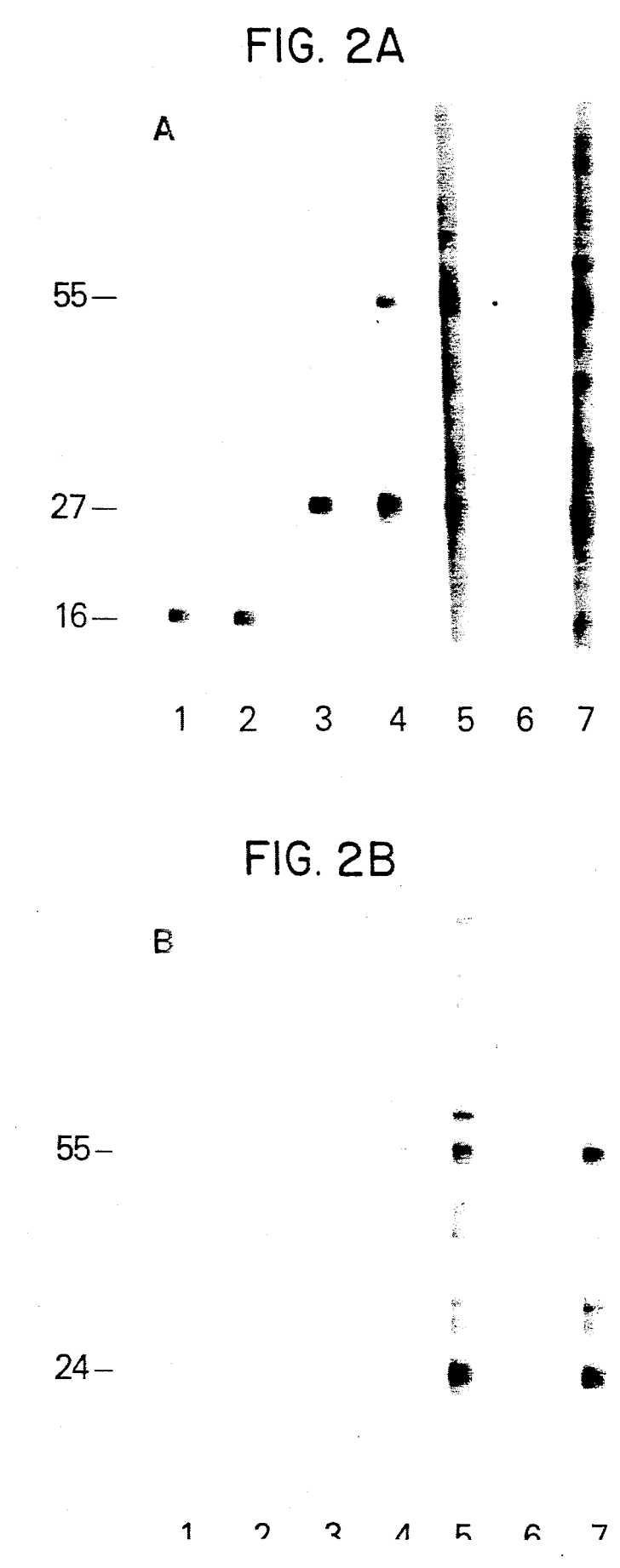
Figure 2C:
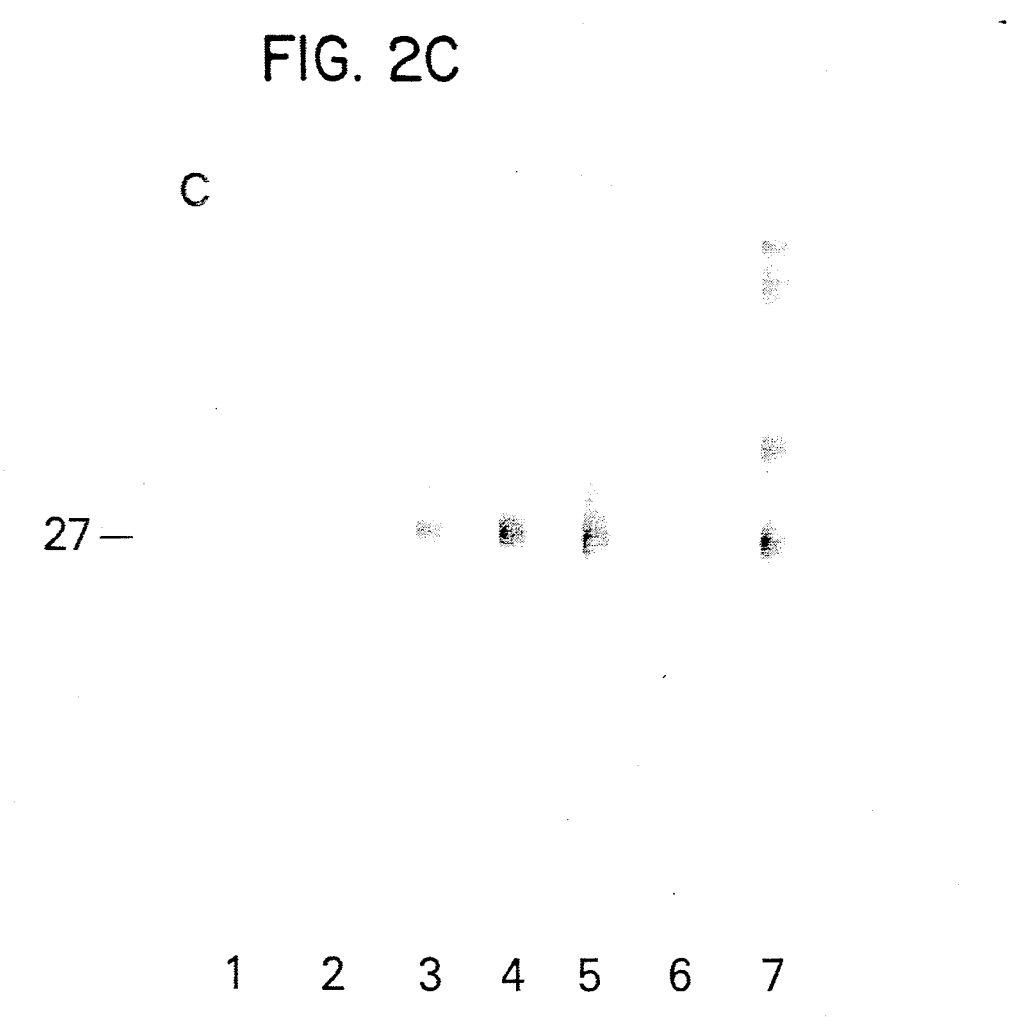

The viral proteins reacting with the different mAbs were identified by immunological blot analysis (FIG. 2). All four mAbs reacted with the gag proteins of HIV-2. Whereas antibodies R5C4 and R5F6 reacted with the MA (p16) protein of HIV-2 (FIG. 2A, lanes 1 and 2). A4F6 and R1C7 reacted specifically with the CA protein (p24) of HIV-2 (FIG. 2A, lanes 3 and 4). All four mAbs reacted with a gag precursor protein p55 of HIV-2, which is sometimes packaged in the virion. The cross-reactivity found with immunofluorescence was confirmed by immunological blot analysis. Antibody R1C7, which is specific for CA of HIV-2, also reacted with the CA proteins of HIV-1 and SIV (FIG. 2 B and C, lane 4).

A4F6 reacted with p24 of HIV-2 and SIV (STLV-III$_{AGM}$), whereas R5C4 and R5F6, which are specific for the MA protein of HIV-2, did not cross-react with HIV-1 or SIV. Again, all the mAbs recognizing the gag proteins reacted with the precursor p55.

The data presented herein clearly demonstrate multiple utilities of the mAbs of the present invention. For example, the broad reactivity of R1C7 mAb allows the detection of any member of the AIDS-related retrovirus family in tissues, body fluids or cultured cells, while the specificity of R5C4 or R5F6 only for HIV-2 isolates, provides a differentiation feature of the present invention.

A diagnostic kit for detecting any member of the HIV-1, HIV-2 and SIV family of retroviruses comprises a container containing synthetic peptide composed of amino acid residues 226–237 of the HIV-1 gag gene. A positive immunological reaction between this peptide and a biological sample indicates the presence of a retrovirus in said sample.

A method for detecting the presence of and identifying the retroviral strain, comprises the steps of:
(a) First, isolating the viral strain from a subject suspected of having been infected with a retrovirus;
(b) then reacting the isolated viral strain from step (a) or a component thereof, with R1C7 antibodies, a positive reaction being indicative of the presence of retroviral infection;
(c) then reacting another sample of the same isolated strain or a component thereof as in step (a) separately with each of A4F6, R5C4 and R5F6 antibodies, a positive reaction with R5C4 and R5F6 being indicative of the presence of HIV-2, and a negative reaction with R5C4 and R5F6, but a positive reaction with A4F6 being indicative of the presence of SIV. Table 1 shows how various tests could be utilized to identify and differentiate between various AIDS-related viruses.

It is understood that the examples and embodiments described herein are for illustrative purposes only and that various modifications or changes in light thereof will be suggested to persons skilled in the art and are to be included within the spirit and purview of this application and scope of the appended claims.

TABLE 1

Immunofluorescence reactivity of mAbs with different HIV-1, HIV-2, and SIV isolates

| Virus isolate | R1C7(CA) | A4F6(CA) | R5C4(MA) | R4F6(MA) | M33(MA) | BT3(CA) |
|---|---|---|---|---|---|---|
| HIV-1 | | | | | | |
| HTLV-III$_B$ | + | − | − | − | + | + |
| HTLV-III$_{MN}$ | + | − | − | − | + | + |
| HTLV-III$_{RF}$ | + | − | − | − | + | + |
| HTLV-III$_{CC}$ | + | − | − | − | + | + |
| HTLV-III$_{Rutz}$ | + | − | − | − | + | + |
| HIV-2 | | | | | | |
| HIV-2$_{NIH-Z}$ | + | + | + | + | − | − |
| LK001 ST9 | + | + | + | + | − | − |
| LAV-2$_{Rod}$ | + | + | + | + | − | − |
| SIV | | | | | | |
| STLV-III$_{AGM}$ | + | + | − | − | − | − |
| SIV-251 | + | + | − | − | − | − |
| SIV-309 | + | + | − | − | − | − |
| SIV-142 | + | − | − | − | − | − |
| SIV-157 | + | − | − | − | − | − |
| SIV-186 | + | − | − | − | − | − |
| SMM-5 | + | − | − | − | − | − |
| HTLV-I C91/PL | − | − | − | − | − | − |
| EIAV EFK | − | − | − | − | − | − |

The M33 and BT3 mAbs are directed against HIV-1 core proteins; the remaining mAbs are anti-HIV-2$_{NIH-Z}$ antibodies. The identification of HIV-2 proteins reacting with mAbs is described in FIG. 2. Positive (+) and negative (−) refer to reactivity in an indirect immunofluorescence assay. The positivity of cells infected with different HIV-1, HIV-2, and SIV isolates was in the range of 10–90%. EIAV, equine infectious anemia virus; EFK, equine fetal kidney cells.

What is claimed is:

1. A hybridoma cell line selected from the group consisting of R1C7 or A4F6.

2. The hybridoma cell line R1C7 according to claim 1.

3. The hybridoma cell line A4F6 according to claim 1.

4. A method for identifying the presence of HIV-1, HIV-2 or SIV in a sample comprising reacting an aliquot of said sample with the monoclonal antibodies produced the hybridoma cell line of claim 2, adding labelled antibodies directed against said monoclonal antibodies, a visible or chemical reaction being indicative of the formation of a specific immune complex between said monoclonal antibodies and HIV-1, HIV-2 or SIV, said specific immune complex indicating the presence of HIV-1, HIV-2 or SIV.

5. A method of determining whether at least one of HIV-1, HIV-2 and SIV are present in a sample comprising the steps of:
a) reacting an aliquot of a sample suspecting of containing one or more of the viruses with A4F6, R5C4, R5F6, and BT3 monoclonal antibodies, each of said reactions occurring in a separate container means with a separate antibody with a separate antibody;
b) adding to each container means labelled antibodies directed against the monoclonal antibodies present in said container means;
c) examining each container means for the presence or absence of a visual or chemical reaction such that
a visual or chemical reaction in said container means containing R5C4 and in said container means containing R5F6 indicates the presence of HIV-2 in said sample;
a visual or chemical reaction in said container means containing A4F6, the absence of said reaction in said container means containing R5C4, and the absence of said reaction in said container means containing R5F6, indicates the presence of SIV in said sample;

a visual or chemical reaction in said container means containing BT3, the absence of said reaction in said container means containing A4F6, the absence of said reaction in said container means containing R5C4 and the absence of said reaction in said container means containing R5F6, indicates the presence of HIV-1 in said sample; and a visual or chemical reaction in said container means containing BT3, a visual or chemical reaction in said container means containing R5C4, a visual or chemical reaction in said container means containing R5F6, indicates the presence of HIV-1 and HIV-2 in said sample.

* * * * *